United States Patent [19]

Huwiler et al.

[11] 4,391,979

[45] Jul. 5, 1983

[54] PROCESS FOR THE PREPARATION OF (2-AMINO-THIAZOL-4YL)-ACETIC ACID HYDROCHLORIDE

[75] Inventors: Alfred Huwiler; Leander Tenud, both of Visp, Switzerland

[73] Assignee: Lonza Ltd., Gampel, Valais, Switzerland

[21] Appl. No.: 227,489

[22] Filed: Jan. 22, 1981

[30] Foreign Application Priority Data

Feb. 18, 1980 [CH] Switzerland ......................... 1284/80

[51] Int. Cl.$^3$ .......................................... C07D 277/38
[52] U.S. Cl. .................................... 548/194; 424/270
[58] Field of Search ................ 548/194, 193; 424/270, 424/271

[56] References Cited

U.S. PATENT DOCUMENTS

4,308,391 12/1981 Dowe et al. ........................ 548/194

FOREIGN PATENT DOCUMENTS

| | | |
|---|---|---|
| 2715385 | 11/1977 | Fed. Rep. of Germany . |
| 2806226 | 8/1978 | Fed. Rep. of Germany . |
| 2812625 | 9/1978 | Fed. Rep. of Germany . |
| 2831332 | 2/1979 | Fed. Rep. of Germany . |
| 2390442 | 12/1978 | France . |
| 2381053 | 6/1979 | France . |
| 2384779 | 7/1979 | France . |
| 2384781 | 4/1980 | France . |

*Primary Examiner*—Nicholas S. Rizzo
*Attorney, Agent, or Firm*—Fisher, Christen & Sabol

[57] ABSTRACT

Process for the simplified preparation of (2-amino-thiazol-4-yl)-acetic acid hydrochloride in light-stable form, in high purity and in good yields, by the reaction of thiourea with 4-chloroacetoacetyl chloride.

10 Claims, No Drawings

PROCESS FOR THE PREPARATION OF (2-AMINO-THIAZOL-4YL)-ACETIC ACID HYDROCHLORIDE

BACKGROUND OF THE INVENTION

1. Field of this Invention

This invention relates to a process for the production of (2-aminothiazol-4-yl)-acetic acid hydrochloride from thiourea.

2. Prior Art (2-Aminothiazol-4-yl)-acetic acid and its derivatives constitute side chains of semi-synthetic cephalosporins. In the conventional processes for preparing it and its derivatives, ethyl 4-chloroacetoacetate or ethyl 4-bromoacetoacetate is reacted with thiourea to give ethyl (2-aminothiazol-4-yl)-acetate hydrochloride or hydrobromide, respectively. The free ethyl aminothiazolylacetate is then prepared by neutralizing the hydrochloride or hydrobromide, and is subsequently converted, by hydrolysis, to aminothiazolylacetic acid. The product thus obtained is light-sensitive and relatively easily undergoes decarboxylation in solution to give 2-amino-4-methylthiazole.

BROAD DESCRIPTION OF THIS INVENTION

An object of this invention is to provide a process for preparing (2-aminothiazol-4-yl)-acetic acid hydrochloride in a simple manner. Another object of this invention is to provide a process for preparing light-stable (2-aminothiazol-4-yl)-acetic acid hydrochloride. Other objects and advantages of this invention are set out herein or are obvious herefrom to one ordinarily skilled in the art.

The objects and advantages of this invention are achieved by the process of this invention.

This invention include a process which involves suspending thiourea in water, adding 4-chloroacetoacetyl chloride, which is dissolved in a chlorohydrocarbon, to the suspension at a temperature of 5° to 10° C., and then completing the reaction at a temperature of 25° to 30° C.

The chlorohydrocarbon employed can be, for example, carbon tetrachloride, chloroform or 1,2-dichloroethane, and preferably is methylene chloride. The chlorohydrocarbon is liquid at the process temperatures.

In a preferred embodiment of this invention, the 4-chloroacetoacetyl chloride dissolved in the chlorinated solvent (preferably methylene chloride) is added dropwise, at the rate at which it is consumed, to the thiourea suspended in water.

During the addition the temperature is kept at 5° to 10° C., preferably 7° to 8° C.

The amount of water employed to prepare the initial thiourea suspension is advantageously from 125 to 250 g per mole of thiourea.

4-Chloroacetoacetyl chloride is employed as a solution in a chlorohydrocarbon. Advantageously, 3 to 50 moles of solvent, preferably 8 to 25 moles of solvent, are employed per mole of 4-chloroacetoacetyl chloride.

In a preferred embodiment of this invention, a 4-chloroacetoacetyl chloride solution, which is obtained by chlorinating diketene in a chlorohydrocarbon (preferably methylene chloride) at −10° to −25° C., is used. This solution can be directly employed.

The (2-aminothiazol-4-yl)-acetic acid hydrochloride obtained by the process of this invention is stable both in solution and as a solid, and can accordingly be stored in such forms.

DETAILED DESCRIPTION OF THIS INVENTION

EXAMPLE

To prepare the starting material (namely 4-chloroacetoacetyl chloride) for the present process, 187.7 g of methylene chloride and 18.6 g of diketene are introduced into a double-walled flask and cooled to −25° C. Chlorine is then passed into this solution at a temperature of −20° to −25° C. Parallel thereto, a suspension of 15.2 g of thiourea in 30.0 g of water is prepared in a round-bottomed flask, and is cooled to +5° C.

The thiourea suspension in the apparatus is cooled to +5° to +7° C. The prepared 4-chloroacetoacetyl chloride solution is added dropwise to the suspension in the course of 25 minutes, at +7° to +8° C., from the dropping funnel of the apparatus, with constant stirring. After completion of the addition, stirring is continued for 30 minutes at +5° to +7° C. The cooling bath is then removed and stirring is continued for a further 60 minutes, during which time the temperature rises to +26° to 27° C. The reaction mixture is then placed in a refrigerator in order for the (2-aminothiazol-4-yl)-acetic acid hydrochloride to precipitate.

33.6 g of (2-aminothiazol-4-yl)-acetic acid hydrochloride are isolated as colorless crystals having a melting point of 151.4° to 151.9° C.—this corresponds to a yield of 78.5 percent, based on the diketene employed. The product is light-stable.

What is claimed is:

1. Process for the preparation of (2-aminothiazol-4-yl)-acetic acid hydrochloride comprising suspending thiourea in water, adding 4-chloroacetoacetyl chloride, which is dissolved in a chlorohydrocarbon, to the suspension at a temperature of 5° to 10° C., and then completing the reaction at a temperature of 25° to 30° C., said (2-aminothiazol-4-yl)-acetic acid hydrochloride being in light-stable form, having a high degree of purity, and being stable both in solution and as a solid.

2. The process as claimed in claim 1 wherein the chlorohydrocarbon is methylene chloride.

3. The process as claimed in claim 1 or claim 2 wherein the 4-chloroacetoacetyl chloride, dissolved in the chlorohydrocarbon, is added to the suspension at the rate at which it is consumed.

4. The process as claimed in claim 3 wherein a 4-chloroacetoacetyl chloride solution is used which has been obtained by chlorinating diketene in the chlorohydrocarbon at a temperature of −10° to −25° C.

5. The process as claimed in claim 1 wherein the chlorohydrocarbon is carbon tetrachloride, chloroform or 1,2-dichloroethane.

6. The process as claimed in claim 1 wherein 3 to 50 moles of chlorohydrocarbon are used per mole of 4-chloroacetoacetyl chloride.

7. The process as claimed in claim 1 wherein a 4-chloroacetoacetyl chloride solution is used which has been obtained by chlorinating diketene in the chlorohydrocarbon at a temperature of −10° to −25° C.

8. Process for the preparation of (2-aminothiazol-4-yl)-acetic acid hydrochloride consisting of suspending thiourea in water, adding 4-chloroacetoacetyl chloride, which is dissolved in a chlorohydrocarbon, to the suspension at a temperature of 5° to 10° C., and then completing the reaction at a temperature of 25° to 30° C., said (2-aminothiazol-4-yl)-acetic acid hydrochloride being in light-stable form, having a high degree of purity, and being stable both in solution and as a solid.

9. (2-Aminothiazol-4-yl)-acetic acid hydrochloride prepared by the process of claim 1, said (2-aminothiazol-4-yl)-acetic acid hydrochloride being in light-stable form, having a high degree of purity, and being stable both in solution and as a solid.

10. (2-Aminothiazol-4-yl)-acetic acid hydrochloride prepared by the process of claim 8, said (2-aminothiazol-4-yl)-acetic acid hydrochloride being in light-stable form, having a high degree of purity, and being stable both in solution and as a solid.

* * * * *